(12) United States Patent
Bajpai

(10) Patent No.: US 11,971,401 B2
(45) Date of Patent: Apr. 30, 2024

(54) METHOD FOR RAPID IDENTIFICATION OF PHARMACOLOGICALLY ACTIVE CHEMICAL ENTITIES ASSOCIATED WITH THE EFFICACY OF ETHNOBOTANICAL SUBSTANCES

(71) Applicant: Biological Life, Inc., Simi Valley, CA (US)

(72) Inventor: Mangala P. Bajpai, Simi Valley, CA (US)

(73) Assignee: Biological Life, Inc, Simi Valley, CA (US)

(*) Notice: Subject to any disclaimer, the term of this patent is extended or adjusted under 35 U.S.C. 154(b) by 438 days.

(21) Appl. No.: 16/692,727

(22) Filed: Nov. 22, 2019

(65) Prior Publication Data
US 2020/0088720 A1    Mar. 19, 2020

Related U.S. Application Data

(62) Division of application No. 12/054,129, filed on Mar. 24, 2008, now abandoned.

(51) Int. Cl.
*G01N 33/50*    (2006.01)
*C12Q 1/00*    (2006.01)
*G01N 33/94*    (2006.01)

(52) U.S. Cl.
CPC ......... *G01N 33/5067* (2013.01); *C12Q 1/00* (2013.01); *G01N 33/5038* (2013.01); *G01N 33/5044* (2013.01); *G01N 33/94* (2013.01)

(58) Field of Classification Search
CPC ......... G01N 33/5067; G01N 33/5038; G01N 33/5044
See application file for complete search history.

(56) References Cited

PUBLICATIONS

Ireson et al. Characterization of Metabolites of the Chemopreventative Agent Curcumin in Human and Rat Hepatocytes and in the Rat in Vivo, and Evaluation of Their Ability to Inhibit Phorbol Ester-Induced Prostaglandin E2 Production; Cancer Research, vol. 61 (2001) pp. 1058-1064.*
Barnes et al. Applications of LC-MS in the Study of the Uptake, Distribution, Metabolism and Excretion of Bioactive Polyphenols From Dietary Supplements; Life Sciences, vol. 78 (2006) pp. 2054-2059.*
Lu et al. Comparison of Intrinsic Clearance in Liver Microsomes and Hepatocytes From Rats and Humans: Evaluation of Free Fraction and Uptake in Hepatocytes; Drug Metabolism and Disposition, vol. 34, No. 9 (2006) pp. 1600-1605.*
Gurib-Fakim et al. Biological Activity From Indigenous Medicinal Plants of Mauritius; Pure and Applied Chemistry, vol. 77, No. 1, pp. 41-51. (Year: 2005).*

* cited by examiner

*Primary Examiner* — Jeanette M Lieb
*Assistant Examiner* — Paul C Martin
(74) *Attorney, Agent, or Firm* — Clark A. Puntigam

(57) ABSTRACT

The method includes the steps of performing in-vitro liver, intestinal and/or expressed enzyme assays with selected ethnobotanical substances, for both humans and a variety of animal species, to produce an array of resulting chemical entities, such as metabolites, for the human and the animals. Comparisons are then made between the chemical entities from the human in-vitro studies and the animal in-vitro studies to determine the closest match. The animal with the closest match is then used for an in-vivo study. If a match is present between the animal in-vivo results and the human in-vitro results, the matched chemical entity is isolated or synthesized and then further tested to determine the suitability of the matched chemical entity as a treatment drug.

18 Claims, 4 Drawing Sheets

METHOD FOR RAPID IDENTIFICATION OF PHARMACOLOGICALLY ACTIVE CHEMICAL ENTITIES ASSOCIATED WITH THE EFFICACY OF ETHNOBOTANICAL SUBSTANCES

CROSS REFERENCE TO RELATED APPLICATIONS

Reference is made to parent application Ser. No. 12/054,129, now abandoned.

TECHNICAL FIELD

This invention relates generally to methods of drug discovery and development, and more specifically concerns such a method which is substantially faster in identifying safe and effective drugs produced from ethnobotanical substances than existing methods.

BACKGROUND OF THE INVENTION

In typical modern drug discovery methods, a target biomolecule which causes disease is first identified. Typically, the biomolecule is a protein. The targets are then developed into laboratory-scale assays or screens. The laboratory-scale screens are converted into automated screens for high throughput evaluation of potential drug compounds. High throughput screening involves the testing of many different compounds (compound libraries), chosen from a large array of chemicals for their ability to inhibit or otherwise affect the target disease in some specific desired way. Often, those compound libraries will comprise thousands of chemicals or even more. Those chemicals which look promising, as indicated by the results of the high throughput screening process, are then further screened to produce the most promising leads/candidates. These leads/candidates are first tested with in-vitro assays, and then in-vivo in laboratory animals, to determine if they produce activity against the target disease. A compound which passes this assay testing process will then typically undergo the conventional drug discovery and development process involving various testing procedures and clinical trials.

Such conventional methods involve a substantial amount of time and cost, and often produce commercially nonviable compounds. Hence, it would be desirable to have a drug discovery method which is simpler, more straightforward, less expensive and more reliable in identifying effective disease fighting compounds.

SUMMARY OF THE INVENTION

Accordingly the present invention is a method for identifying medicinally active chemical entities in ethnobotanical substances, comprising the steps of: (1) providing an ethnobotanical natural substance occurring naturally in nature, the ethnobotanical substance comprising an existing land or marine plant source identified as having an active agent associated with a medicinal effect on humans, wherein the land or marine plant source consists of roots or fruits or seeds or bark or leaves; (2) performing an in-vitro assay with the ethnobotanical substance with one or more of the following: (a) human intestinal preparations and (b) human liver preparations, thereby producing an array of human chemical entities; (3) performing an in-vitro assay of said ethnobotanical substance using one or more of the following: (a) animal intestinal preparations and (b) animal liver preparations from at least one selected animal species to produce an array of animal chemical entities; (4) comparing the array of human chemical entities with the array of animal chemical entities; (5) determining any matches between the human chemical entities in the array of human chemical entities and the animal chemical entities in the array of animal chemical entities to identify a matched animal species; (6) performing an in-vivo dosing of the ethnobotanical substance with the matched animal species; (7) obtaining a biological fluid sample from the matched animal species following the in-vivo dosing; (8) performing an analysis of the biological fluid sample from the matched animal species to determine the presence of chemical entities in the biological fluid sample; (9) comparing the chemical entities in the biological fluid sample with the human chemical entities from the in-vitro assay and determining any matches between the chemical entities in the biological fluid sample with the human chemical entities from the in-vitro assay wherein the matched chemical entities are identified as potentially medicinally active chemical entities; wherein in one embodiment, the human and animal in-vitro assays are intestinal microsomal assays, in another embodiment liver hepatocytes assays and in another embodiment enzyme expression assays.

BEST MODE FOR CARRYING OUT THE INVENTION

The present method makes use of established in-vitro study processes, including for example metabolic processes, as well as other processes, to identify chemical entities, both primary and secondary, which are responsible for the efficacy of ethnobotanical substances, i.e. medicines. The term "chemical entities" as used herein includes, but is not limited to, metabolites and other chemical entities produced by body action as well as chemical entities present in the ethnobotanical substances themselves and/or extracts thereof. These in-vitro study processes can include various study designs utilizing enzymatic preparations, such as human and animal intestinal and/or liver preparations (microsomes, hepatocytes, liver slices, etc.) as well as human and animal enzyme expression preparations, such as lymphoblast and baculovirus-insect cell expression preparations, to produce an array of human and animal chemical entities.

It is well known that ethnobotanical substances, i.e. natural substances, including extracts thereof, from both land and marine plant sources, such as roots, fruits, seeds, bark and leaves, etc. have been used throughout human history for successful treatment of various diseases and maladies. In the recent past, ethnobotanical data has been carefully evaluated in an effort to discover new chemical compounds, i.e. active agents, associated with the ethnobotanicals which are responsible for the medicinal effect observed in naturally occurring ethnobotanical substances.

The presumption to this point has been that the active agent resides in the extracts of the ethnobotanical substances, which can be obtained by traditional fractionation methods. However, numerous extracts obtained from ethnobotanical substances which have seemingly had the potential of producing the same significant medicinal effect as the ethnobotanical substances themselves, have had a high failure rate relative to identifying the active agents in the ethnobotanical substances, despite sophisticated instrumentation and advanced analytical techniques.

The present method is based on a concept disclosed herein, specifically that the advantageous medicinal effect of various ethnobotanical substances is more likely due to chemical entities, such as for example, metabolites, which are the product of liver enzyme and/or intestinal oxidation or other bodily function which occurs when the ethnobotanical substance is ingested by the human user, and hence not necessarily from the chemical entity present per se in the ethnobotanical extract. The present method is designed to rapidly identify the chemical entities which may be responsible for the efficacy of the ethnobotanical substances. Further, the method may identify a library of novel compounds for further structure activity relationship evaluation.

Figure 3A:
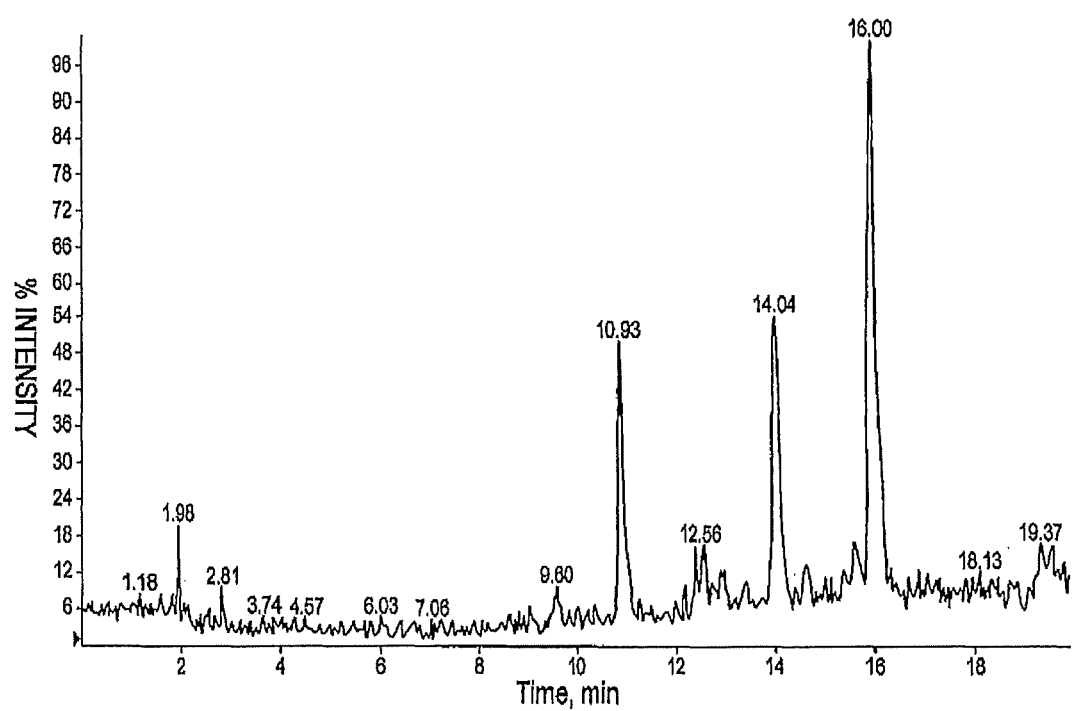
FIG. 3A is a chart of a high performance liquid chromatograph mass spectrometer (HPLC-MS) output for a chemical compound.
Figure 3B:
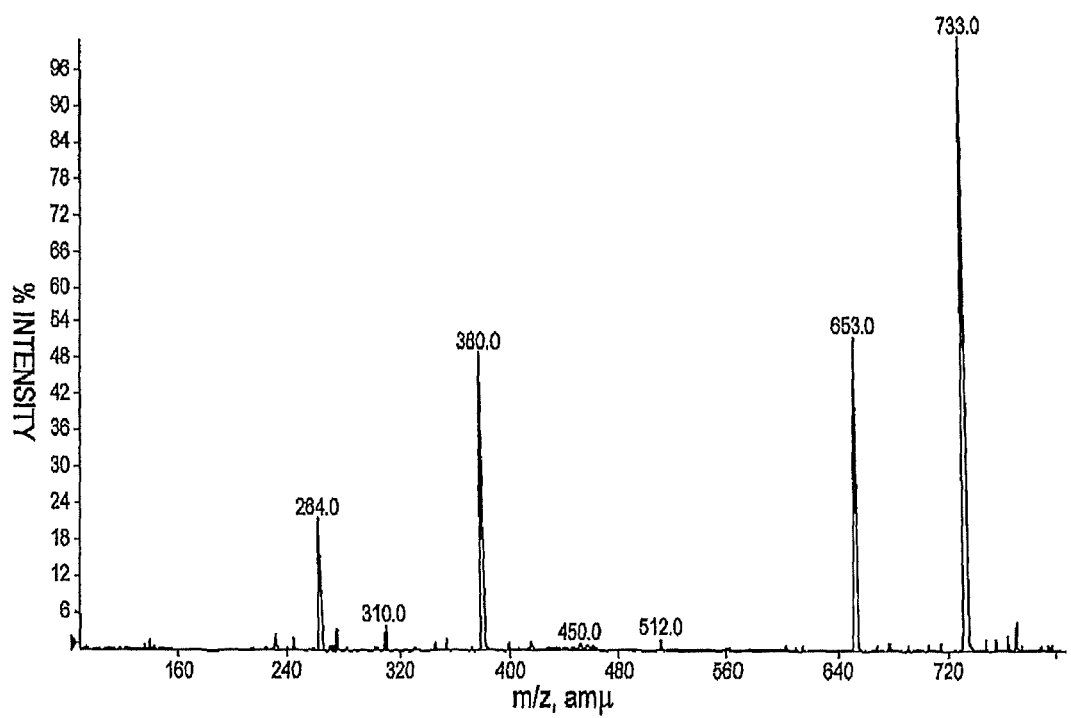
FIG. 3B is another chart for the chemical compound of FIG. 3A.

In a first step in one embodiment (FIG. 1) of the process, shown in block 12 thereof, human liver microsomal (HLM) assays, as one example, are used to produce in-vitro profiles, i.e. identification, of resulting chemical entities, such as metabolites, from a selected ethnobotanical substance. The term ethnobotanical substance used herein includes extracts thereof. In addition to the liver microsomal assays, further examples of specific preparations which could be used for this in-vitro step include intestinal and/or other liver preparations as well as human enzyme expression preparations, such as lymphoblast and baculovirus-insect cell expression preparations. A liquid chromatograph mass spectrometer (LC-MS) and/or gas chromatograph mass spectrometer (GC-MS) analysis of the samples from the in-vitro assays is then performed. An example of an LC-MS display from an in-vitro assay for a given chemical compound is shown in FIG. 3 for illustration.

Figure 1:
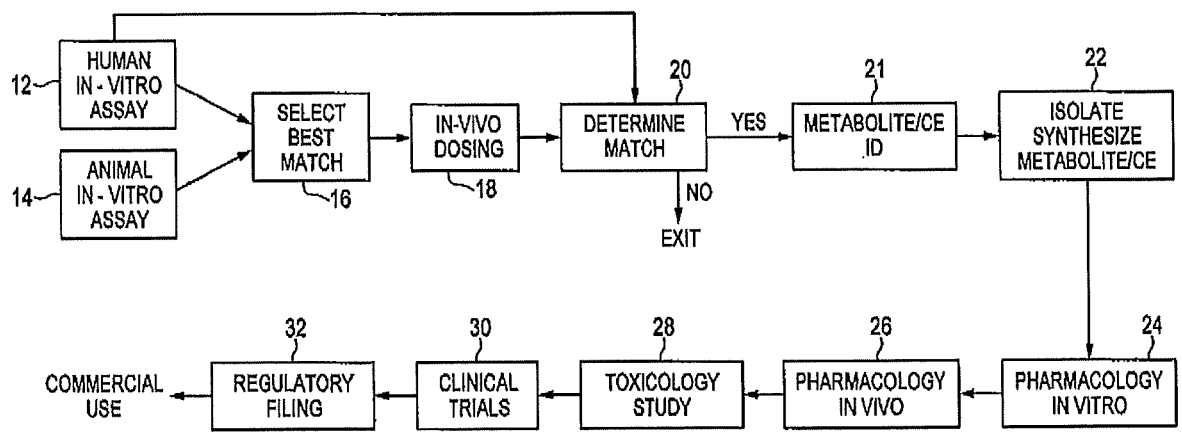
FIG. 1 is a block diagram which sets forth the individual steps in the method disclosed herein.

The same assays are also performed in-vitro with preparations from various animal species, shown in block 14 in FIG. 1. Animal intestinal and/or liver preparations as well as animal enzyme expression preparations could be used as well as the preferred liver microsomes, like that used for the human in-vitro assay. The possible animal species include, for example, among others, mice, rats, dogs, monkeys, etc. While testing of a variety of animals is preferred, it should be understood that animal in-vitro testing could be accomplished with just one animal species. It should also be understood that in the method of FIG. 1, the above two in-vitro assay steps could be reversed in sequence and the claims herein interpreted accordingly.

The in-vitro results from the selected animal or animals are then compared with the in-vitro results from the human in-vitro assays. The best matches from one or more animal species are then selected (block 16) for in-vivo dosing with the ethnobotanical substance, as shown in block 18. The various terms match, matches or best match as used herein and in the claims refer to results having a similar chromatographic or mass spectrometric profile, or equivalent standard. One skilled in the art can identify a match as defined above for the purposes of carrying out the present method by applying such a standard, as it is well understood by those skilled in the art. The meaning of the term "similar profiles" can include, for instance, similarly positioned peaks in the chromatographic or spectrometric data. Also, the term "similar metabolic profile" is well understood as a suitable standard and can be used for establishing a match in appropriate situations in the present method. This match determination of the data can be done by a human, utilizing pre-established standards in accordance with the above considerations, or the data can be compared automatically with the use of a computer program utilizing conventional correlation methods to determine whether or not any match is sufficiently close to proceed with in-vivo testing. A combined manual and automatic determination can also be used.

The matched animal species then undergoes a typical dosing (animal feeding) study (block 18). The dosing will, for example, comprise the following protocol and feeding schedule. The ethnobotanical material/substance (e.g. leaves, seeds, roots, fruits, etc.) is administered to the animal in an oral dosing regimen in a capsule, paste, ground material or extract form, using commercially available formulation vehicles, such as described in the publication titled *Drugs—From Discovery to Approval*; Rick Ng; Wiley-Lip. 2004.

Following the in-vivo feeding program, selected biological fluid samples, such as, for example, blood (whole blood or plasma), urine, feces, bile, etc., are collected and analyzed, using an LC-MS and/or GC-MS or other equivalent analytical techniques to display the presence of the chemical entities, such as metabolites, present in the selected biological fluid. This is followed by a comparison with the results obtained from the in-vitro human testing. This is shown at block 20 in FIG. 1. A comparison is then made to again determine matches, using the above-described chromatographic or mass spectrometric similar profile comparison or equivalent standard. Again, such a comparison to determine a match for the purposes of this method is within the knowledge of one skilled in the art, and can be done by a human operator, using pre-established standards, or it can be done automatically, using a machine with a computer program, or by a combination of manual and automatic steps.

Those (one or more) chemical entities, such as, for example, but not limited to, metabolites, which satisfy the matching/comparison criteria, if any, are identified as potential active chemical entities which could possibly be responsible for the efficacy of the original ethnobotanical substance occurring in nature which has some known medicinal effect, shown for example as metabolite ID in block 21, although it could be other chemical entities (CE) as well.

At this point, well-known methods are used to either isolate or synthesize the match-determined chemical entity (which could, for instance, be a metabolite or it could be another chemical entity). This is shown at block 22 in FIG. 1. These are well-known commercial methods, such as described, for example, in *Modern Methods of Organic Synthesis*: W. Carruthers and kin Coldham; Cambridge University Press, 2004.

Following synthesis/isolation of the match-determined metabolite(s) or other chemical entity, conventional drug development methods are utilized. This includes in-vitro or in-vivo pharmacology studies (blocks 24, 26) as well as toxicology studies (block 28). These studies can be done in sequence or in parallel. Metabolites and perhaps other chemical entities are likely to satisfy the pharmacology evaluation criteria, since the metabolites and other identified chemical entities typically will have known safety and activity profiles. Following the pharmacology and toxicology studies, human clinical trials will be conducted. The conduct of human clinical trials is well known. Human clinical trials are discussed in many texts and publications.

One example, for illustration, is *A Guide to Clinical Drug Research*: A. Cohen & J. Posner; Springer, 2$^{nd}$ Ed. 2000. A regulatory filing (block 32) follows, with subsequent commercial use.

Figure 2:
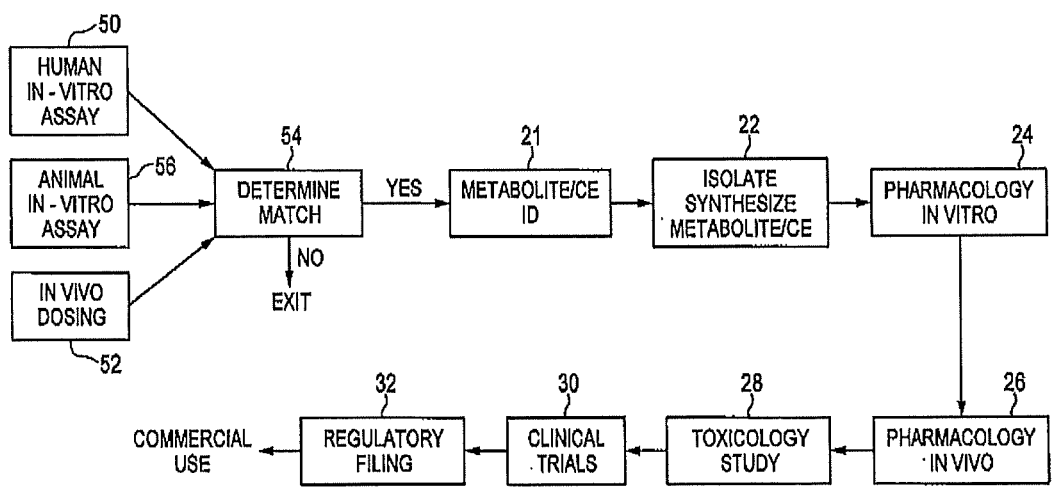
FIG. 2 is a block diagram showing alternative embodiments to the method of FIG. 1.

In another embodiment, shown in FIG. 2, human in-vitro assays (block 50) can be compared with the results of in-vivo dosing (block 52) of one or more animal species and a match, if any, determined (block 54). In this embodiment, the step of animal in-vitro assays (block 56) is not used. Any match-determined chemical entities can then be synthesized, as shown at block 22. With this embodiment, and the next embodiment, the initial individual steps of human in-vitro assays and animal in-vivo dosing can be accomplished in any sequence. The remaining steps in FIG. 2 are identical to the steps in FIG. 1.

FIG. 2 shows yet another embodiment of the method disclosed herein. In this embodiment, like that immediately above, human in-vitro assays (block 50) can be compared with the results of in-vivo dosing (block 52) of one or more animal species. If there is no match, then in-vitro assays are done for the same animal, and the in-vitro animal results are compared with in-vitro human results (block 56). The in-vitro animal assays of the ethnobotanical substances use intestinal and/or liver and/or enzyme preparations from the same animal. Any match-determined chemical entities, including for example, but not limited to, metabolites, can then be synthesized, at block 22, as shown in FIG. 1. The remaining steps in FIG. 2 are identical to the steps in FIG. 1.

The advantage to the above-described methods is that they eliminate a substantial amount of time and effort used in current drug discovery/development methods which involve target selection, validation, high throughput screening and medicinal chemistry evaluations. The steps of the above methods of identifying chemical entities which have a high probability of efficacy are rapid and reliable, involving relatively little time and expense. Upon identification of the high probability chemical entities, traditional pharmacology studies and toxicology studies, followed by clinical trials, can be utilized.

It is advantageous that those chemical entities which ultimately are identified and enter into the conventional pharmacological and toxicology studies have a high probability of success in effectiveness. Further, they also may have a high probability of success in toxicology testing, since the chemical entities, such as metabolites, resulting from the ethnobotanical substances (including extracts thereof) often already have a satisfactory safety profile. Following success with clinical trials, the new drug can then be submitted to regulatory agencies for marketing authorization and subsequent commercial use.

Although a preferred embodiment of the invention has been disclosed here for the purposes of illustration, it should be understood that various changes, modifications and substitutions may be incorporated in the embodiment without departing from the spirit of the invention, which is defined by the claims which follow.

What is claimed is:

1. A method for identifying medicinally active chemical entities in ethnobotanical substances, comprising the steps of:
   (1) providing an ethnobotanical natural substance occurring naturally in nature, the ethnobotanical substance comprising an existing land or marine plant source identified as having a previously unidentified active agent associated with a medicinal effect on humans in the form of previously unidentified medicinally active chemical entities which are the product of bodily function which occurs when the ethnobotanical substance is ingested by the human user, wherein the land or marine plant source consists of roots or fruits or seeds or bark or leaves;
   (2) performing an in-vitro assay with the ethnobotanical substance with one or more of the following: (a) human intestinal preparations and (b) human liver preparations, thereby producing an array of human chemical entities;
   (3) performing an in-vitro assay of said ethnobotanical substance using one or more of the following: (a) animal intestinal preparations and (b) animal liver preparations from at least a plurality of animal species to produce an array of animal chemical entities;
   (4) performing an in-vivo dosing of the ethnobotanical substance with an animal species from the plurality of animal species having animal chemical entities which match the human chemical entities;
   (5) obtaining a biological fluid sample from the animal species of (4) following the in-vivo dosing thereof;
   (6) performing an analysis of the biological fluid sample of (5) to determine the presence of chemical entities in the biological fluid sample; and
   (7) wherein any matches between the biological fluid sample chemical entities of the animal species of (5) and the human chemical entities from the in-vitro assay are potentially medicinally active chemical entities associated with the efficacy of the ethnobotanical substance.

2. The method of claim 1, including the further step of synthesizing or isolating those in-vitro human and in-vivo animal chemical entities that match for use in follow-on studies to confirm the suitability of the matched chemical entities as a treatment drug.

3. The method of claim 2, wherein the follow on studies include pharmacology in-vitro studies, pharmacology in-vivo studies and toxicology studies to determine the suitability of the matched chemical entities.

4. The method of claim 1, wherein matches are accomplished using pre-established standards.

5. The method of claim 4, wherein matches are carried out automatically.

6. The method of claim 4, wherein matches are carried out manually.

7. The method of claim 4, wherein matches are carried out with a combination of automatic and manual steps.

8. The method of claim 1, wherein the human and animal in-vitro assays are liver microsomal assays.

9. The method of claim 1, wherein the human and animal in-vitro assays are intestinal microsomal assays.

10. The method of claim 1, wherein the human and animal in-vitro assays are liver hepatocytes assays.

11. The method of claim 1, wherein the human and animal in-vitro assays are enzyme expression assays.

12. The method of claim 1, wherein the biological fluid is whole blood and/or plasma.

13. The method of claim 1, wherein the medicinally active chemical entities are metabolites.

14. The method of claim 1, wherein the human and animal in-vitro assays are liver microsomal assays, wherein the chemical entities are metabolites and wherein the biological fluid is whole blood or plasma.

15. The method of claim 1, wherein the biological fluid testing includes the use of LC-MS and/or GC-MS data.

16. A method for identifying medicinally active chemical entities in ethnobotanical substances, comprising the steps of:
  (1) providing an ethnobotanical natural substance occurring naturally in nature, the ethnobotanical substance comprising an existing land or marine plant source identified as having a previously unidentified active agent associated with a medicinal effect on humans, in the form of previously unidentified medicinally active chemical entities which are the product of bodily function which occurs when the ethnobotanical substance is ingested by the human user, wherein the land or marine plant source consists of roots or fruits or seeds or bark or leaves;
  (2) performing an in-vitro assay with the ethnobotanical substance with one or more of the following: (a) human intestinal preparations and (b) human liver preparations to produce an array of human chemical entities;
  (3) performing an in-viva dosing of a plurality of animal species with said ethnobotanical substance;
  (4) obtaining a biological fluid sample from the plurality of animal species following the in-vivo dosing;
  (5) performing an analysis of the biological fluid samples to determine the presence of chemical entities in the biological fluid samples;
  (6) wherein, if there is not a match between the chemical entities from the biological fluid samples and the array of human chemical entities from the in-vitro assay, then steps (7)-(9) are performed;
  (7) performing an in-vitro assay of said ethnobotanical substance using one or more of the following: (a) animal intestinal preparations and (b) animal liver preparations from the plurality of animal species to produce an array of animal chemical entities; and
  (8) wherein the matched chemical entities are potentially medicinally active chemical entities associated with efficacy of the ethnobotanical substance.

17. The method of claim 16, including the step of synthesizing or isolating those in-vitro human and in-vivo animal and in-vitro animal chemical entities which match for use in follow-on studies to confirm the suitability of said matched chemical entities as a treatment drug.

18. The method of claim 16, wherein the human and animal in-vitro assays are liver microsomal assays, wherein the chemical entities are metabolites and wherein the biological fluid is whole blood or plasma.

* * * * *